United States Patent [19]

Perregaard et al.

[11] Patent Number: 5,393,761
[45] Date of Patent: Feb. 28, 1995

[54] 3-ARYLINDOLE COMPOUNDS

[75] Inventors: Jens K. Perregaard, Jaegerspris; Kim Andersen, Copenhagen-V., both of Denmark

[73] Assignee: H. Lundbeck A/S, Copenhagen-Valby, Denmark

[21] Appl. No.: 131,438

[22] Filed: Oct. 4, 1993

Related U.S. Application Data

[63] Continuation of Ser. No. 734,299, Jul. 18, 1991, abandoned.

[30] Foreign Application Priority Data

Jul. 30, 1990 [DK] Denmark .................. 1811/90

[51] Int. Cl.⁶ ............... A61K 31/445; C07D 401/04; C07D 403/04
[52] U.S. Cl. ............... 514/323; 514/252; 514/253; 514/254; 514/339; 544/373; 546/201; 546/257; 546/273
[58] Field of Search ............. 546/201, 257, 273; 544/393, 394, 54, 55, 96, 97, 295, 369, 370; 514/252, 254, 339, 253, 323, 326

[56] References Cited

U.S. PATENT DOCUMENTS

| | | | |
|---|---|---|---|
| 4,139,634 | 2/1979 | Pigerol ............ | 544/373 |
| 4,710,500 | 12/1987 | Perregaard et al. ...... | 514/254 |
| 5,071,859 | 12/1991 | Kundsen ............ | 546/207 |

FOREIGN PATENT DOCUMENTS

| | | | |
|---|---|---|---|
| 247250 | 9/1987 | Australia ............ | 544/373 |
| 0135781 | 4/1985 | European Pat. Off. ... | C07D 401/04 |
| 2811031 | 9/1978 | Germany ............ | C07D 403/04 |

OTHER PUBLICATIONS

Adachi et al. *Chem. Pharm. Bull.* 33(5):1826–1835.
Meunier et al. "Neurotransmitteurs Bases Neurobiologiques et Pharmacologiques", Masson, Paris, 1992, pp. 226–227.

*Primary Examiner*—Celia Chang
*Attorney, Agent, or Firm*—Darby & Darby

[57] ABSTRACT

3-Arylindole or 3-arylindazole derivatives having formula:

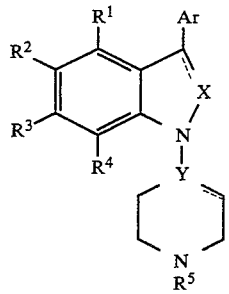

wherein Ar is optionally substituted phenyl or a heteroaromatic group; $R^1$–$R^4$ are independently selected from hydrogen, halogen, alkyl, alkoxy, hydroxy, nitro, alkylthio, alkylsulphonyl, alkyl- or dialkylamino, cyano, trifluoromethyl, or trifluoromethylthio;

the dotted lines designate optional bonds;

X is N or a group $CR^6$ wherein $R^6$ is hydrogen, halogen, trifluoromethyl or alkyl, or X is $CH_2$; Y is N or CH, or Y is C;

$R^5$ is hydrogen, cycloalkyl, cycloalkylmethyl, alkyl or alkenyl, optionally substituted with one or two hydroxy groups, or $R^5$ is a group taken from structures 1a and 1b:

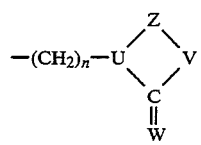

or

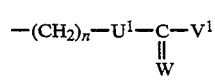

wherein n is an integer from 2–6; W is O or S; U is N or CH; Z is $-(CH_2)_m-$, m being 2 or 3, $-CH=CH-$, 1,2-phenylene or $-COCH_2-$ or $-CSCH_2-$; V is O, S, (Abstract continued on next page.)

$CH_2$, or $NR^7$; $U^1$ is O, S, $CH_2$ or $NR^8$; and $V^1$ is $NR^9R^{10}$, $OR^{11}$, $SR^{12}$ or $CR^{13}R^{14}R^{15}$, and $R^7$–$R^{15}$ are independently hydrogen, alkyl, alkenyl, cycloalkyl or cycloalkylalkyl; may be prepared by methods known per se. The compounds are selective centrally acting 5-$HT_2$-antagonists in the brain and are useful in treatment of anxiety, agression, depression, sleep disturbances, migraine, negative symptoms of schizophrenia, drug-induces Parkinsonism and Parkinson's disease.

10 Claims, No Drawings

3-ARYLINDOLE COMPOUNDS

This is a continuation of application Ser. No. 07/734,299, filed Jul. 18, 1991, now abandoned.

The present invention relates to novel 3-arylindole or 3-arylindazole derivatives and their acid addition salts with selective and long lasting central serotonin $S_2$ (5-hydroxytryptamine-2; 5-HT$_2$) antagonistic activity, to methods for preparing such compounds, to medicaments comprising such compounds as an active ingredient, and to the beneficial use of these derivatives in the treatment of CNS disorders such as anxiety, agression, depression, sleep disturbances, migraine, negative symptoms of schizophrenia, and Parkinson's disease with a low degree of undesired side effects.

The novel indole and indazole derivatives of the present invention are represented by the following formula:

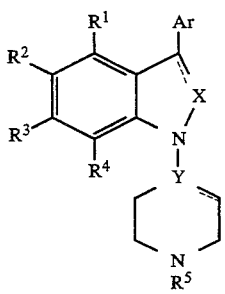

I wherein Ar is phenyl optionally substituted with one or more substituents selected from halogen, lower alkyl, lower alkoxy, hydroxy, trifluoromethyl, and cyano, or Ar is 2-thienyl, 3-thienyl, 2-furyl, 3-furyl, 2-pyridyl, 3-pyridyl, or 4-pyridyl;

$R^1$–$R^4$ are independently selected from hydrogen, halogen, lower alkyl, lower alkoxy, hydroxy, nitro, lower alkylthio, lower alkylsulphonyl, lower alkyl- or dialkylamino, cyano, trifluoromethyl, or trifluoromethylthio;

the dotted line emanating from X in the ring system designates an optional bond; when said dotted line indicates a bond, X is nitrogen or a group $CR^6$ wherein $R^6$ is hydrogen, halogen, trifluoromethyl or lower alkyl; when the dotted line indicates no bond, X is $CH_2$; the dotted line, emanating from the Y; indicates an optional bond; when it does not indicate a bond Y is N or CH; and when it indicates a bond Y is C;

$R^5$ is hydrogen, or cycloalkyl, cycloalkylalkyl, lower alkyl or lower alkenyl, optionally substituted with one or two hydroxy groups, or $R^5$ is a group taken from structures 1a and 1b:

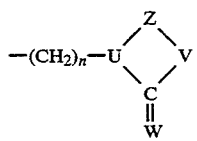

1a.

or

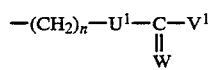

1b.

wherein n is an integer of 2–6 inclusive;

W is oxygen or sulphur;

U is nitrogen or CH;

Z is —(CH$_2$)$_m$—, m being 2 or 3, or Z is 1,2-phenylene optionally substituted with halogen or trifluoromethyl or Z is —CH=CH—,—COCH$_2$— or —CSCH$_2$—; V is oxygen, sulphur, CH$_2$, or NR$^7$, wherein R$^7$ is hydrogen or lower alkyl or alkenyl, cycloalkyl or cycloalkylalkyl optionally substituted with one or two hydroxy groups;

U$^1$ is oxygen, sulphur, CH$_2$ or a group NR$^8$, wherein R$^8$ is hydrogen or lower alkyl or alkenyl, cycloalkyl or cycloalkylalkyl optionally substituted with one or two hydroxy groups; and V$^1$ is NR$^9$R$^{10}$, OR$^{11}$, SR$^{12}$ or CR$^{13}$R$^{14}$R$^{15}$,where each of R$^9$–R$^{15}$ may be independently selected from among the R$^8$-substituents;

provided that R$^5$ may not be methyl when R$^1$–R$^4$ each are hydrogen, X and Y are CH and Ar is phenyl.

Stereoisomers, prodrugs and pharmaceutically acceptable salts of the compounds of formula I are also embraced by the invention.

The term "lower alkyl" is intended to mean a straight or branched alkyl group having from one to four carbon atoms, inclusive such as methyl, ethyl, n-propyl, isopropyl, n-butyl, sec-butyl, etc. Lower alkoxy, lower alkylthio, lower alkylsulfonyl, lower alkylamino and lower dialkylamino similarly designate such groups wherein the alkyl moiety is a lower alkyl group as defined above.

Lower alkenyl is intended to mean an alkenyl group containing from 2 to 4 carbon atoms, inclusive for example ethenyl, 1-propenyl, 2-butenyl, etc.

Cycloalkyl means cycloalkyl having from three to eight carbon atoms inclusive.

Halogen means fluoro, chloro, bromo or iodo.

The term "indicate an optional bond" is intended to mean that the dotted lines may or may not represent a bond, i.e. that the rings may or may not have a double bond in the positions of the dotted lines in Formula I.

The Z groups —COCH$_2$— and —CSCH$_2$— may be incorporated in the ring of the structure 1a in both directions.

The acid addition salts of the invention are pharmaceutically acceptable salts of the compounds of Formula I formed with non-toxic acids. Exemplary of such organic salts are those with maleic, fumaric, benzoic, ascorbic, embonic, succinic, oxalic, bis-methylenesalicylic, methanesulfonic, ethanedisulphonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids, as well as the 8-halotheophyllines, for example 8-bromo-theophylline. Exemplary of such inorganic salts are those with hydrochloric, hydrobromic, sulfuric, sulfamic, phosphoric and nitric acids.

Prodrugs of the present invention may be conventional esters with available hydroxy groups, or in particular if the compound is a compound of the general formula I wherein R$^5$ is a group of the structure 1a wherein V is NH or the structure 1b where U$^1$ is NH and/or V$^1$ is NHR$^{10}$ they may exist as prodrugs in which said nitrogen atom is acylated with a group

wherein A is O, S or NR$^a$ with R$^a$ being hydrogen, lower alkyl, or phenyl optionally substituted with one or more substituents selected from the group comprising halogen, trifluoromethyl, lower alkyl, lower alkoxy, lower alkylthio and cyano;

B is a group R$^b$ which is alkyl or alkenyl containing from one to twentyfour carbon atoms inclusive, or cycloalkyl or cycloalkylalkyl, optionally substituted with one or two hydroxy groups, phenyl optionally substituted with one or more substituents selected from the group comprising halogen, trifluoromethyl, lower alkyl, lower alkoxy, lower alkylthio, or cyano; or B is QR$^{b'}$, wherein Q is O or S and R$^{b'}$ is one of the substituents defined for R$^b$ above; or B is NR$^c$R$^d$, wherein R$^c$ and R$^d$ independently are either hydrogen or one of the substituents defined for R$^b$ above.

Although the latter prodrugs are not esters, they have been found to decompose properly in order to release the compound of the invention over a desired prolonged period of time when administered parenterally as a depot formulation in an appropriate oil, such as peanut oil, sesame oil, cotton seed oil, corn oil, soy bean oil, olive oil, coconut oil (e.g. Viscoleo®), etc., or synthetic esters of fatty acids and glycerol or propyleneglycol.

Only one 3-arylindole or 3-arylindazole derivative substituted in the 1-position with a piperidinyl, piperazinyl or tetrahydropyridyl group is known from the prior art.

1-(1-methyl- 4-piperidinyl)-3-phenylindole is disclosed in Adachi et al., Chem. Pharm. Bull., 33(5), 1826–1835, (1985), as an intermediate in the synthesis of 2-acyl-N-(1-methyl-4-piperidinyl)aniline. Nothing is disclosed or suggested as regards the pharmacological properties of said compound.

On the other hand indole or indazole derivatives having an aryl substituent in the 1position and a tetrahydropyridyl, piperidinyl or piperazinyl group in the 3 position have been disclosed in a number of patents.

DE Offentlegungsschrift No. 2811031 (Laboratories Sauba S.A.) relates to 1-(optionally subst. phenyl)-3-((4-alkyl or aryl)-piperazin-1-yl)-indole derivatives stated to have ant-inflammatory activity.

EP-A2 224919 (Fujisawa Pharmaceutical Co., Ltd.) discloses 1-phenyl-3-(4-(thiazolylalkyl)piperazin-1-yl)indole derivatives as antiallergy agents.

DE Offenlegungsschrift No. 1695604 (Pfizer Corporation) describes 1-phenyl-3(optionally 1-benzyl or 1-methyl substituted 4-piperidinyl)-2-indolones having antidepressant effects.

EP-A 0 135 781 and U.S. Pat. Nos. 4,670,447, 4,758,668 and 4,853,470 all generically relate to a very broad class of 1-aryl-3-piperidylindazoles alleged to have analgesic and antipsychotic and in some of the patents also antidepressant effects. Antipsychotic effects are shown by the apomorphine climbing assay which is a test for classical neuroleptic activity, i.e. dopamine antagonism, and antidepressant effects are shown in the tetrabenazine ptosis test for a few compounds.

EP-A 0 281 309 and US Pat. No. 4,831,031 disclose 3-[4-(heterocycloethyl (or -butyl))piperazin-1-yl]indazoles substituted in the 1-position with trifluoromethylphenyl and claimed to be useful as antipsychotics as shown in the apomorphine climbing test.

European Patent Publication No. 0 302 423 relates to 1-phenyl-3-(1-piperazinyl)-1H-indazoles claimed to be useful as analgesics, anticonvulsants and antidepressants, the antidepressant effects again shown in the tetrabenazine ptosis test in mice. Only results for a few compounds showing quite weak effects are given.

From our own US Pat. No 4,710,500 (corresponding to EP patent No 0200323) 1-aryl-3-(1,2,3,6-tetrahydropyridin-4-yl)-, 1-aryl-3-(4-piperidinyl)- and 1-aryl-3-(1-piperazinyl)-indole derivatives are known. The compounds are claimed to be potent and long-lasting dopamine antagonists, and accordingly to be useful in the treatment of psychoses and additionally to be strong 5-HT$_2$ antagonists indicating effects in the treatment of depression, negative symptoms of schizophrenia and neuroleptic-induced extrapyramidal side effects and cardiovascular diseases. Some of the compounds are selective 5-HT$_2$ antagonists in vivo.

Previously evidence of various clinical effects of 5-HT$_2$ antagonists have been presented. For example reference may be made to the following:

The selective 5-HT$_2$ antagonist ritanserin has been shown to be an antidepressant and to improve depressive symptoms of schizophrenia (E. Klieser, W. H. Strauss; Pharmacopsychiat. 21 (1988), pp. 391–393) and it has been demonstrated to exert effects in an animal test reminiscent of anxiolytic drug activity (F. C. Colpart et al.; Psychopharmacology (1985)86; 45–54). Furthermore ritanserin has been shown to improve the quality of sleep (P. A. J. Janssen; Pharmacopsychiat. 21 (1988), 33–37).

Furthermore it is generally believed that 5-HT is involved in migraine attacks. The links between 5-HT and migraine attacks are several and they suggest a number of mechanisms whereby 5-HT may be involved (Scrip Report; "Migraine-Current trends in research and treatment"; PJB Publications Ltd.; May 1991). Various 5-HT$_2$ antagonists are in clinical trials as antimigraine agents, such as sergolexole (c.f. for example Pharma Projects, May 1991, 1359–1365).

Studies of the mixed serotonin and dopamine receptor antagonist setoperone indicate that blockade of 5-HT$_2$ receptors may be related to improvement of negative symptoms of schizophrenia (Ceulemans et al., Psychopharmacology (1985) 85,329–332).

Finally, ritanserin has been found to relieve neuroleptic-induced parkinsonism (Bersani et al.; Clinical Neuropharmacology, 13, No. 6 (1990), 500–506).

Surprisingly, it has now been found that the novel indole or indazole derivatives of the present invention are selective 5-HT$_2$ antagonists with prolonged activity, and accordingly are useful in the treatment of anxiety, agression, depression, sleep disturbances, migraine, negative symptoms of schizophrenia, drug-induced Parkinsonism and Parkinson's disease substantially without causing neurological side effects.

The compounds of the present invention are selective, and most of them very selective, antagonists of the 5-HT$_2$ receptor, measured as the ratio between the dopamine D-2 receptor and the 5-HT$_2$ receptor antagonistic activities. Only a few compounds with such a selectivity profile are known from the prior art. Such compounds include ritanserin, seganserin, ICI 169369, ICI 170809, sergolexole and MDL 11939, which compounds are very different in chemical structure from the present compounds.

A preferred subgroup of compounds are those wherein X is a CR$^6$ group; most preferably those wherein R$^2$ and/or R$^6$ are other than hydrogen.

Preferably, Ar is phenyl optionally substituted with halogen, most preferably 4-fluorophenyl;

R$^5$ is a group

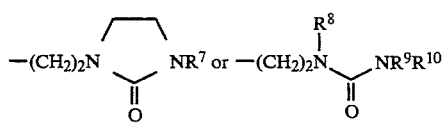

wherein R$^7$, R$^8$, R$^9$ and R$^{10}$ independently are selected from hydrogen, lower alkyl or alkenyl; R$^2$ is selected from halogen, —CF$_3$, and —CH$_3$; R$^3$ is selected from H, halogen, —CF$_3$, and —CH$_3$; and R$^1$ and R$^4$ are H.

Particularly preferred compounds are:

5-Chloro-3-(4-fluorophenyl)-1-[1-[2-(3-methylimidazolidin-2-on-1-yl)ethyl]-4-piperidyl]-1H-indole, 3-(4-Fluorophenyl)-1-[1-[2-(imidazolidin-2-on-1-yl)ethyl]-4-piperidyl]-5-methyl-1H-indole, 3-(4-Fluorophenyl)-5-methyl-1-[1-[2-[3-(2-propyl)imidazolidin-2-on-1-yl]ethyl]-4-piperidyl-1H-indole, 2,5-Dimethyl-3-(4-fluorophenyl)-1-[1-[2-(imidazolidin-2-on-1-yl)ethyl]-1,2,3,6-tetrahydropyridin-4-yl]-1H-indole, 2,5-Dimethyl-3-(4-fluorophenyl)-1-[1-[2-(imidazolidin-2-on-1-yl)ethyl]-4-piperidyl]-1H-indole, 2,5-Dimethyl-3-(4-fluorophenyl)-1-(1-methyl-4-piperidyl)-1H-indole, and 1-[1-[2-(1,3-Dimethyl-1-ureido)ethyl]-4-piperidyl]-3-(4-fluorophenyl)-5-methyl-1H-indole.

In another aspect the present invention provides a pharmaceutical preparation comprising at least one compound of the Formula I as an active ingredient together with a pharmaceutically acceptable carrier or diluent.

The compounds of the Formula I and the pharmaceutically acceptable acid addition salts thereof may be administered by any suitable route, for example orally in the form of tablets, capsules, powders, syrups, etc., or parenterally in the form of solutions for injection.

Suitable pharmaceutical preparations may be prepared by methods well known in the art. Conveniently, the compounds of the invention are administered in unit dosage form containing said compound in an amount of about 0.10–100 mg, preferably about 1–50 mg.

The total daily dose usually ranges from about 0.1 to 500 mg of the active compound of the invention. In a further aspect the present invention provides the use of a compound of the Formula I for the manufacturing of a pharmaceutical preparation for the treatment of CNS disorders.

The present invention also provides a method for treating CNS disorders comprising administration of a compound having the general Formula I or an acid addition salt thereof to a patient suffering from such a disease.

Finally, the present invention provides a method for the preparation of a derivative having the general Formula I, which method comprises:

a) reacting a compound of the following formula:

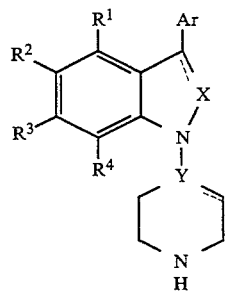

wherein R$^1$,R$^2$,R$^3$,R$^4$,X, Y, Ar and the dotted lines are as defined above, with a lower alkyl halide, alkyl mesylate or tosylate, with an epoxide of the formula

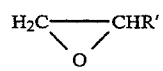

wherein R' is hydrogen, methyl or ethyl or with a halide of the general formula

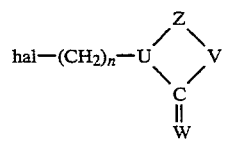

or

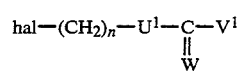

wherein n, W,U,V,Z,V$^1$ and U$^1$ are as defined above;

b) reacting a compound of following formula:

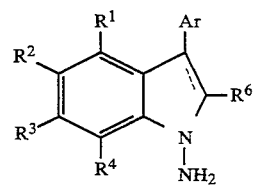

wherein R$^1$,R$^2$,R$^3$,R$^4$,R$^6$, Ar and the dotted line are as defined above, with a compound of the general formula R$^5$N(CH$_2$CH$_2$hal)$_2$     V in which R$^5$ is as defined above and hal is halogen;

c) reducing the indole ring of a compound of the general formula

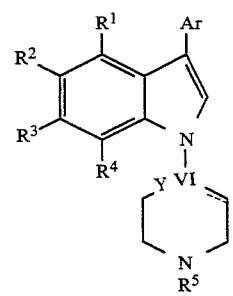

wherein $R^1$–$R^5$, Ar, Y and the dotted line are as defined above, to a dihydroindole ring;

d) reducing the double bond in the tetrahydropyridyl ring in a compound of the formula:

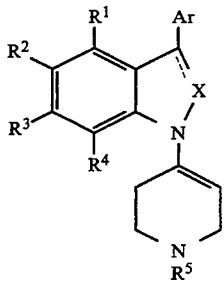

VII wherein $R^1$–$R^5$, X, Ar and the dotted line are as defined above;

e) reducing the pyridinium ring in a compound of following formula:

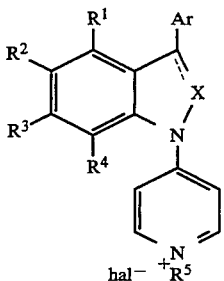

VIII wherein $R^1$–$R^5$, X, Ar and the dotted line are as defined above except that $R^5$ may not be hydrogen, and hal is halogen, to a tetrahydropyridine ring;

f) reducing the pyridinium ring in a compound of the above Formula VIII or the pyridyl ring of a compound of formula XIV (below) to a piperidine ring;

g) reducing the carbonyl group of a compound of the following formula:

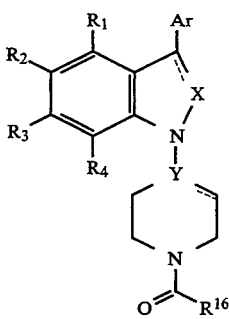

IX wherein $R^1$–$R^4$,X,Y,Ar and the dotted lines are as previously defined and $R^{16}$ is hydrogen, lower alkyl or lower alkoxy;

h) acylating an aminoalkyl derivative of the following formula:

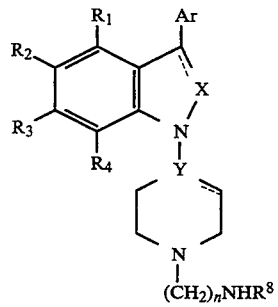

X wherein $R^1$–$R^4$,X,Y,Ar,$R^8$,n and the dotted lines are as defined above, with an acylating agent such as a carboxylic acid halogenide, anhydride or mixed anhydride, or a carbamyl or thiocarbamyl chloride, an isocyanate, isothiocyanate, or a substituted chloroformate;

i) ringclosure reaction of an intermediate ethylene or propylene diamine derivative of the following formula:

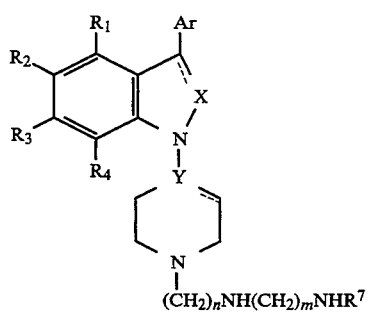

XI wherein $R^1$–$R^4$,$R^8$,n,X,Y,Ar and the dotted lines are as defined above and m is 2 or 3, with phosgene, thiophosgene or carbondisulphide to form a substituent of the structure 1a; or j) reducing a carboxylic acid or carboxylic acid derivative of the following formula:

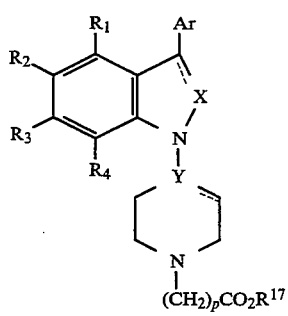

XII wherein $R^1$–$R^4$,X,Y,Ar and the dotted lines are as previously defined, $R^{17}$ is hydrogen or lower alkyl and p is 1,2 or 3;

and then, if desired:

acylating a compound prepared in one of the methods (a) to (j) having the formula I in which $R^5$ is a structure 1a or 1b wherein V is NH, or $V^1$ is $NHR^{10}$ or $U^1$ is NH with an acylating agent, or esterifying an available hydroxy group in a compound of formula I in order to obtain a prodrug;

convening a compound prepared in one of methods (a) to (j)in a pharmaceutically acceptable acid addition salt thereof; or resolving an optically active compound of formula I prepared in one of methods (a) to (j)in optically active isomers thereof.

In method (a) the reaction is conveniently performed at 20°-120° C. in an aprotic solvent such as acetone or methyl isobutyl ketone in the presence of free base (e.g. $K_2CO_3$ or triethylamine) and the starting compounds of Formula II are prepared as described below.

3-aryl-1-(4-piperidyl)indoles and 3-aryl-1-(4-piperidyl)indazoles are prepared as shown in the following reaction scheme:

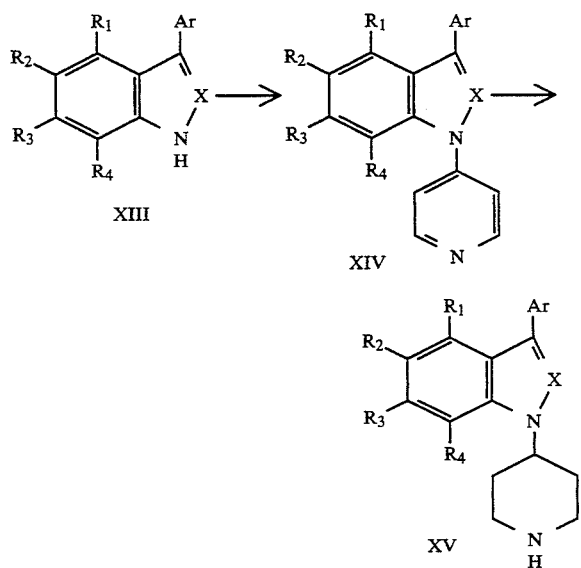

wherein $R^1$-$R^4$, $R^6$ and Ar are as defined above.

An 3-arylindole or 3-arylindazole of the Formula XIII is arylated with 4-chloro- or 4-bromopyridine in NMP, DMF, HMPA or DMSO with potassium carbonate as base and catalyzed by copper, copper(I) iodide or copper(I) bromide at 150°-210° C. The 3-aryl-1-(4-pyridyl)indole or 3-aryl-1-(4-pyridyl)indazole of Formula XIV thus obtained is reduced to the 3-aryl-1-(4-piperidyl)indole or 3-aryl-1-(4-piperidyl)indazole of the Formula XV with hydrogen at low pressure (3 ato.) in the presence of platinum.

3-Arylindoles, which are unsubstituted in the 2-position, are prepared from the corresponding 2-cyano-3-arylindoles or 3-arylindole-2-carboxylic esters by alkaline or acidic hydrolysis followed by decarboxylation in NMP or quinoline with copper catalysis. The 2-cyano-3-arylindoles and 3-arylindole-2-carboxylic esters used are prepared either from the corresponding anilines by Japp-Klingemann reaction followed by Fischer indole synthesis or from the corresponding 2-benzoylanilines according to modified literature procedures (Morooka et al, *Synthesis*, 1978, 445, Hughes et al, *J. Proc. Roy. Soc. N. S. Wales*, 1939,72, 209 and C. D. Jones, *J. Org. Chem.*, 1972, 37, 3624).

2-Substituted 3-arylindoles are prepared either from the corresponding 2-benzoylanilines or by Fischer indole synthesis from the corresponding substituted phenyl hydrazones (e.g. (4-fluorophenyl)acetone (4-methylphenyl)hydrazone) according to modified literature procedures (Greuter et al, *Helv. Chem. Acta*, 1974, 57, 281 and Yamamoto et al, *Chem. Pharm. Bull.*, 1968, 16, 2313).

3-Arylindazoles are prepared either from the corresponding 2-benzoylanilines or by heating the corresponding 2-chloro- or bromobenzophenone hydrazone with base, according to modified literature procedures (Dziewonski et al., *Bull. Intern. Acad. Polonaise, Casse Sci. Math. Nat.*, 1935A, 333 (*Chem. Abstr.*, 1936, 30, 1972) and Gladstone et al., *J. Chem. Soc.*, 1965, 3048).

2-Halo-3-aryl-1-(4-piperidyl)indoles are prepared from the corresponding 3-aryl-1-(4-piperidyl)indoles, in which the piperidine nitrogen is protected by a suitable aminoprotective group (e.g. methyl or 2,2,2-trichloroethyl carbamate), by halogenation with an halogenation reagent such as N-bromosuccinimide, N-chlorosuccinimide or bromine in an inert solvent (e.g. $CCl_4$ or acetic acid) according to modified literature procedures (Hino et al., *Tetrahedron*, 1974, 30, 2123), followed by deprotection of the piperidine nitrogen by standard methods which are obvious to the chemist skilled in the art.

In method (b) the reaction is performed by refluxing a compound of Formula IV with a compound of Formula V and a strong base (e.g. sodium amide)in an inert solvent, e.g. toluene. The starting compounds of Formula IV are prepared by reacting the corresponding 3-arylindoles, prepared as described above, with hydroxylamine-O-sulphonic acid and strong base (e.g. potassium tert.-butoxide) in a polar aprotic solvent (e.g. DMF).

In method (c) the reduction is conveniently performed with a complex hydride (e.g. sodium borohydride) in acidic solution (e.g. trifluoroacetic acid).

In method (d) the reduction is suitably carried out at a low hydrogen pressure (3 ato.) in the presence of platinum or palladium or by refluxing a compound of formula VII with ammonium formate and palladium in a water miscible solvent (e.g. ethanol).

In method (e) the reduction is expediently carried out with a complex hydride (e.g. sodium borohydride in methanol) whereas the reduction in method (f) preferably is performed by catalytic hydrogenation with platinum as a catalyst. The starting compounds of Formula VIII are prepared by quaternizing a 1-(4-pyridyl)-3-arylindole or 1-(4-pyridyl)-3-arylindazole, prepared as described above, with a lower alkyl halide or a halide of the general Formula IIIa or IIIb in MIBK or acetone. The reduction in method (g) is conveniently carried out with lithium aluminum hydride in tetrahydrofuran, or diethyl ether, or with diborane in tetrahydrofuran. Aminoalkyl derivatives of the Formula X (method h) are prepared by alkylating a compound of the Formula II with a halo-nitrile of the following formula: hal$(CH_2)_n$CN in the presence of a base (e.g.. $K_2CO_3$ or triethylamine) in an inert solvent such as acetone, MIBK or toluene at elevated temperature (30°-100° C.). The cyano group may be reduced according to standard procedures using e.g. $AlH_3$, $LiAlH_4$ or $B_2H_6$. The $R^9$ substituent is introduced by direct alkylation or by an acylation/reduction procedure, which is obvious to the chemist skilled in the art. Acylation of the thus obtained amino derivatives is accomplished by addition of an acylating agent at a low temperature (−20°-30° C.) preferably in a chlorinated solvent (dichloromethane, chloroform, or 1,1,1-trichloroethane) and, if necessary, in the presence of a base to neutralize any acidic reaction product formed.

Ethylene or propylene diamines as intermediates for the ringclosure procedure in method (i) are prepared by repeating with appropriate reagents the procedure described for the preparation of the aminoalkyl derivatives used as starting materials in method (h). Generally, heating (80°–150° C.) is required to effect ringclosure with the appropriate carbonyl- or thiocarbonyl precursor compound (phosgene, thiophosgene, carbondisulphide, urea or thiourea).

In method (j) the reduction is conveniently carried out using a complex hydride (e.g. lithium aluminum hydride)in an inert solvent (e.g. diethyl ether). The starting compounds of Formula XII are prepared by reacting a compound of Formula II with a halocarboxylic acid ester of formula hal-$(CH_2)_p CO_2 R^{17}$ in the presence of a base (e.g. $K_2CO_3$ or triethylamine)in an inert solvent such as acetone, MIBK or toluene at elevated temperature (30°–100° C.).

The ω-haloalkyl-2-imidazolidinone alkylating reagents (substructure of structure IIIa) were prepared according to modified literature procedures (see e.g. Johnston, T. P.; McCaleb, G. S.; Montgomery, J. A. The Synthesis of Antineoplastic Agents. XXXII. N-Nitrosureas. *J. Med. Chem.* 1963, 6, 669–681; Ebetino, F. F. Belg. Patent 653421, 1965; *Chem. Abstr.* 1966, 64, 12684; Costeli, J.; Züst, A. Ger. Offen 2035370, 1971; *Chem. Abstr.* 1971, 74, 87985z). Other sidechains of structure IIIa were prepared as stated in the literature.

The acid addition salts of the compounds of the invention are easily prepared by methods well known in the art. The base is reacted with either the calculated amount of organic or inorganic acid in an aqueous miscible solvent, such as acetone or ethanol, with isolation of the salt by concentration and cooling, or with an excess of the acid in an aqueous immiscible solvent, such as diethyl ether or chloroform, with the desired salt separating directly. Of course, these salts may also be prepared by the classical method of double decomposition of appropriate salts.

In the following the invention is further illustrated by way of examples, which in no way may be construed as limiting for the invention.

EXAMPLE 1

3-(4-Fluorophenyl)-1H-indole 2a.

Methyl 3-(4-fluorophenyl)-1H-indole-2-carboxylate 22d (59.6 g) was refluxed in a mixture of methanol(1.5 l) and 2N aqueous NaOH (500 ml) for 3.5 h. The reaction mixture was cooled to room temperature, the solvents were evaporated in vacuo and water (500 ml) was added. The alkaline solution was acidified and the thus formed precipitate was filtered off and dissolved in ethyl acetate (750 ml). The ethyl acetate solution was washed with brine (500 ml) and dried ($Na_2SO_4$). Evaporation of the solvents afforded the crude 4-fluorophenyl-1H-indole-2-carboxylic acid which was used without further purification.

A mixture of the crude indole-2-carboxylic acid (55.0 g), Cu (2.0 g) and quinoline (1.0 l) was refluxed for 2.5 h, cooled and filtered. The filtrate was poured into water (800 ml) and extracted with diethyl ether (2×800 ml). The combined organic phases were succesively washed with 1N hydrochloric acid (4×1.0 l), washed with brine (1.0 l) and dried ($Na_2SO_4$). Evaporation of the solvent in vacuo gave the title compound which was precipitated from diethyl ether. Yield: 43.6 g, mp 98°–100° C.

In a corresponding manner the following indole derivatives were prepared:

5-Chloro-3-(4-fluorophenyl)-1H-indole 1b, mp 81°–83° C.

3-(4-Fluorophenyl)-5-methyl-1H-indole 1c, mp 123°–126° C.

6-Chloro-3-(4-fluorophenyl)-1H-indole 1d, (oil).

5-Fluoro-3-(4-fluorophenyl)-1H-indole 1e, (oil). 3-(4-Fluorophenyl)-5-trifluoromethyl-1H-indole 1f, (oil).

5-Chloro-3-phenyl-1H-indole 1g, mp 84°–86° C.

EXAMPLE 2

3-(4-Fluorophenyl)-1-(4-pyridyl)-1H-indole 2a.

3-(4-Fluorophenyl)-1H-indole 1a (39.3 g), 4-chloropyridine hydrochloride (55.8 g), $K_2CO_3$ (102.8 g), CuBr (15 g) and N-methylpyrrolidinone (1.2 l) were refluxed under stirring for 18 h. The reaction mixture was cooled, poured into water (1.0 l) and extracted with diethyl ether (2×1 l). The combined organic phases were washed with brine (3×1.5 l), dried ($Na_2SO_4$) and treated with activated carbon. Evaporation of the solvent gave the title compound which was crystallized from diethyl ether. Yield: 42.0 g, mp 115°–118° C.

In a corresponding manner the following indole derivatives were prepared:

5-Chloro-3-(4-fluorophenyl)-1-(4-pyridyl)-1H-indole 2b, mp 162°–164° C.

3-(4-Fluorophenyl)-5-methyl-1-(4-pyridyl)-1H-indole 2c, mp 125°–127° C.

5-Fluoro-3-(4-fluorophenyl)-1-(4-pyridyl)-1H-indole 2d, mp 129°–134° C.

6-Chloro-3-(4-fluorophenyl)-1-(4-pyridyl)-1H-indole 2e, mp 194°–198° C.

3-(4-Fluorophenyl)-1-(4-pyridyl)-5-trifluoromethyl-1H-indole 2f, mp 163°–165° C.

5-Chloro-3-phenyl-1-(4-pyridyl)-1H-indole 2g, mp 130°–132° C.

EXAMPLE 3

(intermediates for method a)

6-Chloro-3-(4-fluorophenyl)-1-(4-piperidyl)-1H-indole 3a. 6-Chloro-3-(4-fluorophenyl)-1-(4-pyridyl)-1H-indole 2e (1.8 g) was dissolved in acetic acid (100 ml) and $PtO_2$ (0.2 g) was added. After hydrogenation for 30 h at 3 ato the catalyst was filtered off, the acetic acid was evaporated in vacuo and water (50 ml) was added. The acidic solution was made alkaline (pH>9) with concentrated sodium hydroxide and extracted with ethyl acetate (2×50 ml). The combined organic phases were successively washed with diluted sodium hydroxide (50 ml), washed with brine, and dried ($Na_2SO_4$). Evaporation of the solvent gave 1.5 g of the title compound as an oil.

In a corresponding manner the following indole and indazole derivatives were prepared:

3-(4-Fluorophenyl)-1-(4-piperidyl)-1H-indole 3b, (oil).

5-Chloro-3-(4-fluorophenyl)-1-(4-piperidyl)-1H-indole 3c, (oil).

3-(4-Fluorophenyl)-5-methyl-1-(4-piperidyl)-1H-indole 3d, (oil).

5-Fluoro-3-(4-fluorophenyl)-1-(4-piperidyl)-1H-indole 3e, (oil).

3-(4-Fluorophenyl)-1-(4-piperidyl)-5-trifluoromethyl-1H-indole 3g, (oil).

5-Chloro-3-phenyl-1-(4-piperidyl)-1H-indole 3g, (oil).

6-Chloro-3-(4-fluorophenyl)-1-(4-piperidyl)-1H-indazole 3h, (oil).

3-(4-Fluorophenyl)-1-(4-piperidyl)-5-trifluoromethyl-1H-indazole 3i, (oil).

EXAMPLE 4

(method a)

6-Chloro-3-(4-fluorophenyl)-1-[1-[2-(3-methylimidazolidin-2-on-1-yl)ethyl]-4-piperidyl)-1H-indole, maleate 4a.

A mixture of 6-chloro-3-(4-fluorophenyl)-1-(4-piperidyl)-1H-indole 3a (1.5 g), 1-(2-chloroethyl)-3-methyl-2-imidazolidinon (1.1 g), $K_2CO_3$ (1.0 g), KI (0.5 g) and methyl isobutyl ketone (100 ml) was refluxed for 18 h. The reaction mixture was cooled, poured into water (50 ml) and extracted with ethyl acetate (2×50 ml). The combined organic phases were dried ($Na_2SO_4$) and the solvents were evaporated in vacuo. The remaining oil was purified by column chromatography on silica gel (eluted with ethyl acetate/isopropanol 9:1 containing 4% triethylamine). The title compound was precipitated as its maleate from ethyl acetate. Yield: 1.4 g, mp 110°–112° C.

In a corresponding manner the following indole and indazole derivatives were prepared:

6-Chloro-3-(4-fluorophenyl)-1-[1-[2-(imidazolidin-2-on-1-yl)ethyl]-4-piperidyl]-1H-indole 4b, mp 192°–194° C.

6-Chloro-3-(4-fluorophenyl)-1-[1-[2-[3-(2-propyl)imidazolidin-2-on-1-yl]ethyl]-4-piperidyl]-1H-indole, hydrochloride, hydrate 4c, mp 255°–258° C.

5-Chloro-3-(4-fluorophenyl)-1-[1-[2-(imidazolidin-2-on-1-yl)ethyl]-4-piperidyl]-1H-indole 4d, mp 171°–174° C.

5  -Chloro-3-(4-fluorophenyl)-1-[1-[2-[3-propyl)imidazolidin-2-on-1-yl]ethyl]-4-piperidyl]-1H-indole 4e, mp 161°–164° C.

5-Chloro-3-(4-fluorophenyl)-1-[1-[2-(3-methylimidazolidin-2-on-1-yl)ethyl]-piperidyl]-1H-indole 4f, mp 128°–133° C.

3-(4-Fluorophenyl)-1-[1-[2-(imidazolidin-2-on-1-yl)ethyl]-4-piperidyl]-5-methyl -1H-indole 4g, mp 185°–187° C.

3-(4-Fluorophenyl)-5-methyl-1-[1-[2-[3-(2-propyl)imidazolidin-2-on-1-yl]ethyl]-4-piperidyl]-1H-indole, oxalate 4h, mp 175°–177° C.

3-(4-Fluorophenyl)-5-methyl-1-[1-[2-(3-methylimidazolidin-2-on-1-yl)ethyl]-4-piperidyl]-1H-indole, fumarate 4i, mp 103°–105° C.

3-(4-Fluorophenyl)-5-methyl-1-[1-[2-(2-pyrrolidinon-1-yl)ethyl]-4-piperidyl]-1H-indole, oxalate 4j, mp 120°–122° C.

3-(4-Fluorophenyl)-1-[1-[2-(imidazolidin-2-on-1-yl)ethyl]-4-piperidyl]-1H-indole 4k, mp 172°–173° C.

3-(4-Fluorophenyl)-1-[1-[2-[3-(2-propyl)imidazolidin-2-on-1-yl]ethyl]-4-piperidyl]-1H-indole, hydrochloride, hydrate 4I, mp 242°–244° C.

5-Fluoro-3-(4-fluorophenyl)-1-[1-[2-(imidazolidin-2-on-1-yl)ethyl]-4-piperidyl]-1H-indole 4m, mp 153°–156° C.

5-Fluoro-3-(4-fluorophenyl)-1-[1-[2-[3-(2-propyl)imidazolidin-2-on-1-yl]ethyl]-4-piperidyl]-1H-indole 4n, mp 143°–145° C.

5-Fluoro-3-(4-fluorophenyl)-1-[1-[2-(oxazolidin-2-on-3-yl)ethyl]-4-piperidyl]-1H-indole 4o, mp 123°–125° C.

5-Chloro-3-phenyl-1-[1-[2-(imidazolidin-2-on-1-yl)ethyl]-4-piperidyl]-1H-indole 4p, mp 155°–157° C.

5-Chloro-3-phenyl -1-[1-[2-[3-(2-propyl)imidazolidin-2-on-1-yl]ethyl]-4-piperidyl]-1H-indole 4q, mp 146°–148° C.

2,3-Dihydro-3-(4-fluorophenyl)-1-[1-[2-(imidazolidin-2-on-1-yl)ethyl]-4-piperidyl]-5-fluoro-1H-indole 4r, mp 182°–186° C.

3-(4-Fluorophenyl)-5-methyl-1-[1-(2-propyl)-4-piperidyl]-1H-indole, maleate 4s, mp 162°–163° C.

6-Chloro-3-(4-fluorophenyl)-1-[1-[2-(imidazolidin-2-on-1-yl)ethyl]-4-piperidyl]-1H-indazole 4t, mp 195°–197° C.

3-(4-Fluorophenyl)-1-[1-[2-(imidazolidin-2-on-1-yl)ethyl]-4-piperidyl]-5-trifluoromethyl-1H-indazole 4u, mp 217°–219° C.

3-(4-Fluorophenyl)-1-[1-[2-[3-(2-propyl)imidazolidin-2-on-1-yl]ethyl]-4piperidyl]-5-trifluoromethyl-1H-indole 4v, mp 156°–158° C.

2-Bromo-3-(4-fluorophenyl)-1-[1-[2-(imidazolidin-2-on-1-yl)ethyl]-4-piperidyl]-1H-indole 4x, mp 194°–196° C.

EXAMPLE 5

(intermediates for methods e and f)

4-[2,5-Dimethyl-3-(4-fluorophenyl)-1H-indol-1-yl]-1-[2-(imidazolidin-2-on-1-yl)ethyl]pyridinium iodide 5a.

A mixture of 2,5-dimethyl-3-(4-fluorophenyl)-1-(4-pyridyl)-1H-indole 17a (5.0 g) and 1-(2-iodoethyl)-2-imidazolidinon (7.6 g) and methyl isobutyl ketone (50 ml) was refluxed for 6 h. After cooling to room temperature the precipitated product was filtered off and dried in vacuo at 70° C. overnight. This afforded 6.3 g of the title compound, mp 215°–217° C.

In a corresponding manner the following indole derivatives were prepared:

4-[3-(4-Fluorophenyl)-5-methyl-1H-indol-1-yl]-1-]2-(imidazolidin-2-on-1-yl)ethyl]pyridinium iodide 5b, mp>250° C.

4-[3-(4-Fluorophenyl)-5-trifluoromethyl-1H-indol-1-yl]-1-[2-(imidazolidin-2-on-1-yl)ethyl]pyridinium iodide 5c, mp>250° C.

EXAMPLE 6

(method e)

2,5-Dimethyl-3-(4-fluorophenyl)-1-[1-[2-(imidazolidin-2-on-1-yl)ethyl]-1, 2,3,6-tetrahydropyridin-4-yl]-1H-indole 6a.

4-[2,5-Dimethyl-3-(4-fluorophenyl)-1H-indol-1-yl]-1-[2-(imidazolidin-2-on-1-yl)ethyl]-pyridinium iodide 5a (6.3 g) was suspended in ethanol (100 ml) and sodium borohydride (2.1 g) was added in three portions during 3.5 h. Then the solvent was evaporated in vacuo and water (100 ml) was added. The mixture obtained was extracted with dichloromethane (2×50 ml). The combined organic phases were washed with brine (100 ml) and dried ($MgSO_4$). Evaporation of the solvent gave the title compound as an oil, which was purified by column chromatography on silica gel (eluted with ethyl acetate/ethanol 8:1 containing 4% triethylamine). Yield: 2.5 g, mp 151°–153° C.

In a corresponding manner the following indole derivatives were prepared:

2,5-Dimethyl-3-(4-fluorophenyl)-1-(1-methyl-1,2,3,6-tetrahydropyridin-4-yl)-1H-indole 6b, mp 98°–100° C.

3-(4-Fluorophenyl)-1-[1-[2-(imidazolidin-2-on-1-yl)ethyl]-1,2,3,6-tetrahydropyridin-4-yl]-5-methyl-1H-indole 6c, mp 129°–131° C.

3-(4-Fluorophenyl)-5-methyl-1-(1-methyl-1,2,3,6-tetrahydropyridin-4-yl)-1H-indole, maleate 6d, mp 168°–171° C.

5-Chloro-2-methyl-1-(1-methyl-1,2,3,6-tetrahydropyridin-4-yl)-3-phenyl-1H-indole, oxalate 6e, mp 165°–168° C.

3-(4-Fluorophenyl)-1-[1-[2-(imidazolidin-2-on-1-yl)ethyl]-1,2,3,6-tetrahydropyridin-4-yl]-5-trifluoromethyl-1H-indole 6f, mp 113°–115° C.

EXAMPLE 7

(method d)

2,5-Dimethyl-3-(4-fluorophenyl)-1-[1-[2-(imidazolidin-2-on-1-yl)ethyl]-4-piperidyl]-1H-indole 7a.

Ammonium formate (12 g) was added in small portions during 18 h to a refluxing mixture of 2,5-dimethyl-3-(4-fluorophenyl)-1-[1-[2-(imidazolidin-2-on-1-yl)ethyl]1,2,3,6-tetrahydropyridin-4-yl]-1H-indole 6a (1.9 g), 5% palladium on activated carbon (1 g) and ethanol (50 ml). The reaction mixture was cooled to room temperature and the solvents were evaporated in vacuo. After addition of water the mixture was made alkaline with concentrated NaOH and extracted with ethyl acetate (2×50 ml).The combined organic phases were dried ($Na_2SO_4$) and the solvents were evaporated in vacuo. This afforded the title compound which crystallized from diethyl ether. Yield 0.2 g, mp 188°–190° C.

In a corresponding manner the following indole derivatives were prepared: 3-(4-Fluorophenyl)-1-[1-[2-(imidazolidin-2-on-1-yl)ethyl]-4-piperidyl]-5-trifluoromethyl-1H-indole 7b, mp 182°–186° C 1-[1-[2-(Imidazolidin-2-on-1-yl)ethyl]-4-piperidyl]-2-methyl-3-phenyl-1H-indole 7c, mp 179°–183° C.

EXAMPLE 8

(intermediates for methods e and f)

4-[2,5-Dimethyl-3-(4-fluorophenyl)-1H-indol-1-yl]-1-methylpyridinium, iodide 8a. 2,5-Dimethyl-3-(4-fluorophenyl)-1-(4-pyridyl)-1H-indole 17a (5.0 g), methyl iodide (5 ml) and acetone (100 ml) were heated at 40° C. for 18 h. After cooling to room temperature the precipitated product was filtered off and dried in vacuo at 70° C overnight yield: 6.3 g, mp 217°–219° C.

In a corresponding manner the following indole derivatives were prepared:

4-(5-Chloro-2-methyl-3-phenyl-1H-indol-1-yl)-1-methylpyridinium, iodide 8b, mp 225°–227° C.

4-[3-(4-Fluorophenyl)-5-methyl-1H-indol-1-yl]-1-methylpyridinium, iodide 8c, mp>250° C.

EXAMPLE 9

(method f) 2,5-Dimethyl-3-(4-fluorophenyl)-1-(1-methyl-4-piperidyl)-1H-indole 9a. 4-[2,5-Dimethyl-3-(4-fluorophenyl)-1H-indol-1-yl]-1-methylpyridinium, iodide 8a (3.0 g) was dissolved in acetic acid (75 ml) and $PtO_2$ (0.4 g) was added. After hydrogenation for 2 weeks at 3 ato the catalyst was filtered off, the acetic acid was evaporated in vacuo and water (50 ml) was added. The thus obtained acidic solution was made alkaline (pH>9) with concentrated sodium hydroxide and extracted with ethyl acetate (2×50 ml). The organic phases were successively washed with diluted sodium hydroxide (50 ml), washed with brine and dried ($Na_2SO_4$). Evaporation of the solvent gave 1.3 g of the title compound as an oil, which was purified by column chromatography on silica gel (eluted with ethyl acetate/ethanol 8:1 containing 4% triethylamine) and crystallized from heptane. Yield 0.4 g, mp 110°–112° C.

In a corresponding manner the following indole derivative was prepared: 5-Chloro-2-methyl-3-phenyl-1-(1-methyl-4-piperidyl)-1H-indole 9b, mp 131°–136° C. (decomp.).

EXAMPLE 10

(intermediates for method g)

Methyl 4-[3-(4-fluorophenyl)-5-methyl-1H-indol-1-yl]piperidine-1-carboxylate 10a . A mixture of 3-(4-fluorophenyl)-5-methyl-1-(4-piperidyl)-1H-indole 3d (6.0 g). $K_2CO_3$ (3.0 g) and dichloromethane (50 ml) was cooled to 0°–5° C. and a solution of methyl chloroformate (2.2 g)in dichloromethane (50 ml) was added during 0.5 h. After reaction for further 2 h at room temperature the reaction mixture was washed with water (2×100 ml) and dried ($MgSO_4$). Evaporation of the solvents in vacuo afforded the title compound, which was used without further purification. Yield: 6.7 g, (oil).

In a corresponding manner the following indole derivative was prepared: 2,2,2-Trichloroethyl 4-[3-(4-fluorophenyl)-1H-indol-1-yl]piperidine-1-carboxylate 10b (oil).

EXAMPLE 11

(method g)

3-(4-Fluorophenyl)-5-methyl-1-(1-methyl-4-piperidyl)-1H-indole, fumarate 11a. A solution of the crude methyl 4-[3-(4-fluorophenyl)-5-methyl-1H-indol-1yl]piperidine-1-carboxylate 10a, (6.7 g) in dry tetrahydrofuran (75 ml) was added to a suspension of lithium aluminum hydride (4 g) in dry tetrahydrofuran (75 ml) during 0.5 h and the reaction mixture was refluxed for 1 h. After cooling on an ice bath water (5 ml), 6 N aqueous NaOH (5 ml) and water (10 ml) were added, successively. The precipitate was filtered off, the filtrate was dried ($MgSO_4$) and the solvents were evaporated in vacuo. This afforded the title compound, as an oil, which was precipitated as its fumarate from ethanol. Yield: 1.4 g, mp 170°–172° C.

EXAMPLE 12

(intermediate for method h)

1-[1-(2-Aminoethyl)-4-piperidyl]-3-(4-fluorophenyl)-5-methyl-1H-indole 12a. A solution of 3-(4-fluorophenyl)-5-methyl-1-(4-piperidyl)-1H-indole 3d (20 g), chloroacetonitrile (5.4 g) and triethylamine (7.5. ml) in N-methylpyrrolidinone (125 ml) was heated at 60° C. for 2 h. The reaction mixture was poured into ice (200 g) and extracted with diethyl ether (2×200 ml). The combined organic phases were washed with brine (3×250 ml), dried ($Na_2SO_4$) and the solvents evaporated in vacuo. This afforded the 1-[1-(2-cyanomethyl)-4-piperidyl]-3-(4-fluorophenyl)-5-methyl-1H-indole, as an oil, which was used without further purification. Yield: 22.2 g. To a suspension of aluminum chloride (5.0 g) in dry diethyl ether (200 ml) was added lithium aluminum hydride (5.0 g) at 10°–15° C. Then a solution of the crude cyanomethyl compound in dry tetrahydrofuran (300 ml) was added dropwise during 0.5 h at 10°–15° C. The reaction mixture was refluxed for 2 h, cooled on an ice bath and concentrated aqueous NaOH (25 ml) was added. The inorganic salts were filtered off and the solvent evaporated in vacuo. The remaining oil was dissolved in dichloromethane, dried ($MgSO_4$) and the solvent was evaporated. This afforded the title compound as an oil. Yield: 18.9 g.

EXAMPLE 13

(method h)
1-[1-[2-(3,3-Dimethyl-1-thioureido)ethyl]-4-piperidyl]-3-(4-fluorophenyl)-5-methyl-1H-indole 13a.

A solution of 1-[1-(2-aminoethyl)-4-piperidyl]-3-(4-fluorophenyl)-5-methyl-1H-indole, 12a (5.0 g), N,N-dimethylthiocarbamoylchloride (2.1 g) and triethylamine (5 ml) in dichloromethane (150 ml) was refluxed for 18 h. After cooling to room temperature the reaction mixture was washed with water and dried (MgSO$_4$). Evaporation of the solvent afforded the title compound as an oil which was purified by column chromatography on silica gel (eluted with ethyl acetate containing 4% triethylamine). The title compound precipitated from ethyl acetate and was recrystallized from diethyl ether. Yield: 0.8 g, mp 106°–108° C.

In a corresponding manner the following indole derivative was prepared:
1-[1-[2-(3,3-Dimethyl-1-ureido)ethyl]-4-piperidyl]-3-(4-fluorophenyl)-5-methyl-1H-indole 13b, mp 126°–128° C.

EXAMPLE 14

(intermediate for method h)
1-[1-(N-Methyl-2-aminoethyl)-4-piperidyl]-3-(4-fluorophenyl)-5-methyl-1H-indole 14a A mixture of 1-[1-(2-aminoethyl)-4-piperidyl]-3-(4-fluorophenyl)-5-methyl-1H-indole 12a (8.9 g), K$_2$CO$_3$ (4.2 g) and dichloromethane (80 ml) was cooled to 0°–5° C. and a solution of methyl chloroformate (2.9 g) in dichloromethane (50 ml) was added during 15 min. After reaction for further 2 h at room temperature the reaction mixture was washed with water (2×50 ml), dried (MgSO$_4$) and the solvents were evaporated in vacuo. This afforded the 1-[1-(N-methoxycarbonyl-2-aminoethyl)-4piperidyl]-3-(4-fluorophenyl)-5-methyl-1H-indole, as an oil, which was used without further purification. Yield: 8.8 g.

A solution of the crude 1-(1-(N-methoxycarbonyl-2-aminoethyl)-4-piperidyl]-3-(4-fluorophenyl)-5-methyl-1H-indole (8.8 g) in dry tetrahydrofuran (75 ml) was added to a suspension of lithium aluminum hydride (2 g) in dry tetrahydrofuran (75 ml) during 15 min and the reaction mixture was refluxed for 1.5 h. After cooling on an ice bath water (4 ml), 4N aqueous NaOH (2.5 ml) and water (10 ml) were added, succesively. The precipitate was filtered off, the solution was dried (Na$_2$SO$_4$) and the solvents were evaporated. This afforded the title compound, as an oil Yield: 6.9 g.

EXAMPLE 15

(method h)
1-[1-[2-(1,3-Dimethyl-1-ureido)ethyl]-4-piperidyl]-3-(4-fluorophenyl)-5 -methyl-1H-indole, hydrochloride 15a.

A mixture of 1-(1-(N-methyl-2-aminoethyl)-4-piperidyl]-3-(4-fluorophenyl)-5-methyl-1H-indole 14a (6.9), methyl isocyanate (2.1 g) and K$_2$CO$_3$ (4 g) in methyl isobutyl ketone (150 ml) was refluxed for 6 h. After cooling to room temperature water (100 ml) was added and the mixture was extracted with ethyl acetate (2×100 ml). The combined organic phases were washed with brine and dried (MgSO$_4$). Evaporation of the solvent afforded the title compound as an oil which was purified by column chromatography on silica gel (eluted with ethyl acetate/ethanol 4:1, containing 4% triethylamine). The title compound was precipitated as its hydrochloride from diethyl ether. Yield: 0.9 g, mp 88°–90° C.

EXAMPLE 16

(method j)
3-(4-Fluorophenyl)-1-[1-(2-hydroxyethyl)-4-piperidyl]-5-methyl-1H-indole, oxalate 16a.

A solution of ethyl bromoacetate in acetone was added during 15 min to a mixture of 3-(4-fluorophenyl)-5-methyl-1-(4-piperidyl)-1H-indole 3d (5.0 g), K$_2$CO$_3$ (2.5 g) and acetone (100 ml) at room temperature. After another 2 h the solvents were evaporated, water was added and the mixture was extracted with ethyl acetate (2×100 ml). The combined organic phases were washed with brine and dried (Na$_2$SO$_4$). Evaporation of the solvent afforded the crude methyl 4-[3-(4-fluorophenyl)-5-methyl-1H-indol-1-yl]1-piperidinacetate (6.0 g), which was used without further purification.

A solution of the crude methyl ester (6.0 g) in tetrahydrofuran (50 ml) was added to a suspension of lithium aluminum hydride (1.2 g) in dry tetrahydrofuran (50 ml) and the mixture was refluxed for 1 h. After cooling on ice bath, water (1.5 ml) and 4N aqueous NaOH (1.5 ml) were added. The precipitate was filtered off and the filtrate was dried (Na$_2$SO$_4$). Evaporation of the solvents afforded the title compound (4.2 g) as an oil which was purified by column chromatography on silica gel (eluted with ethyl acetate containing 4% triethylamine). The title compound precipitated as its oxalate from acetone. Yield: 0.09 g, mp 81°–83° C.

EXAMPLE 17

2,5-Dimethyl-3-(4-fluorophenyl)-1-(4-pyridyl)-1H-indole 17a.

2,5-Dimethyl-(4-fluorophenyl)-1H-indole 24a (50 g), 4-bromopyridine, hydrochloride (80 g), K$_2$CO$_3$ (90 g), CuBr (10 g) and N-methylpyrrolidone (750 ml) were refluxed under stirring for 18 h. The reaction mixture was cooled, poured into water (1.0 l) and extracted with diethyl ether (2×750 ml). The combined organic phases were washed with brine (3×1 l), dried (Na$_2$SO$_4$) and treated with activated carbon. Evaporation of the diethyl ether afforded the title compound (29.8 g) which was purified by column chromatography on silica gel (eluted with ethyl acetate/heptane 3:1). The title compound crystallized from diethyl ether. Yield: 20.5 g, mp 172°–174° C., In a corresponding manner the following indole and indazole derivatives were prepared:
5-Chloro-2-methyl-3-phenyl-1-(4-pyridyl)-1H-indole 17b, mp 158°–160° C.
6-Chloro-3-(4-fluorophenyl)-1-(4-pyridyl)-1H-indazole 17c, (oil). 3-(4-Fluorophenyl)-1-(4-pyridyl)-5-trifluoromethyl-1H-indazole 17d, (oil).

EXAMPLE 18

(method c)
2,3-Dihydro-5-fluoro-3-(4-fluorophenyl)-1-(4-piperidyl)-1H-indole 18a To a solution of 5-fluoro-3-(4-fluorophenyl)-1-(4-piperidyl)-1H-indole 3e (2 g) in trifluoroacetic acid (30 ml) was added sodium cyanoborohydride (1 g). After 2 h reaction at room temperature the solvent was evaporated in vacuo and ethyl acetate (50 ml) was added. The mixture was washed twice with aqueous 2N sodium hydroxide (50 ml) and dried (Na$_2$SO$_4$). Evaporation of the solvent in vacuo afforded the crude product which was used without further purification. Yield: 1.5 g (oil).

In a corresponding manner the following indole derivative was prepared: 2,3-Dihydro-3-(4-fluorophenyl)-1-[1-[2-(imidazolidin-2-on-1-yl)ethyl]-4-piperidyl]-5-methyl-1H-indole 18b, mp 180°–185° C.

EXAMPLE 19

(intermediate for method b)

1-Amino-3-(4-fluorophenyl)-5-methyl-1H-indole 19a.

Potassium tert-butoxid (7.5 g) was added to a solution of 3-(4-fluorophenyl)-5-methyl-1H-indole 1c (15 g) in DMF during 15 min at 0°–5° C. Then a suspension of potassium hydroxylamine-O-sulphonate in DMF (prepared by addition of potassium tert-butoxid (7.5 g) to a suspension of hydroxylamine-O-sulphonic acid (7.6 g) in DMF (100 ml) during 0.5 h at 0°–5° C.) was added slowly at 0°–5° C. After reaction at 0° C. for 1 h the mixture was poured into ice, and extracted with diethyl ether (2×250 ml). The combined organic phases were washed with brine (3×250 ml) and dried ($Na_2SO_4$). Evaporation of the solvents afforded the title compound which was purified by column chromatography on silica gel (eluted with ethyl acetate/heptane 1:3) and crystallized from diethylether. Yield: 4.3 g, mp 116°–120° C.

EXAMPLE 20

(method b)

3-(4-Fluorophenyl)-5-methyl-1-(1-methylpiperazin-4-yl)-1H-indole 20a.

To a mixture of 1-amino-3-(4-fluorophenyl)-5-methyl-1H-indole 19a (1 g) and toluene (20 ml) was added a 50% suspension of sodium amide in xylene (1.0 ml). After reaction for 15 min at room temperature a solution of N,N-bis(2-chloroethyl)methylamine (0.8 g) in toluene was added slowly and the mixture was refluxed for 3 h. After cooling to room temperature, the solvents were evaporated in vacuo and water (100 ml) was added. The mixture was extracted with ethyl acetate (2×50 ml) and the combined organic phases were dried ($Na_2SO_4$). Evaporation of the solvents in vacuo afforded the title compound, which was purified by column chromatography on silica gel (eluted with ethyl acetate/ethanol 4:1 containing 4% triethylamine) and crystallized from heptane. Yield: 0.5 g, mp 105°–107° C.

EXAMPLE 21

1-[1-[2-(3-Acetylimidazolidin-2-on-1-yl)ethyl]-4-piperidyl]-3-(4-fluorophenyl)-5-methyl-1H-indole, oxalate 21a (Prodrug).

To a mixture of 3-(4-fluorophenyl)-1-[1-[2-(imidazolidin-2-on-1-yl)ethyl]-4-piperidyl]-5-methyl-1H-indole 4g (3 g), $K_2CO_3$ (1.3 g) and toluene (50 ml) was added a solution of acetyl chloride (0.6 ml) in toluene (5 ml) during 10 min at 0°–5° C. After reaction for further 18 h at room temperature the reaction mixture was filtered, the solvent was evaporated in vacuo and ethyl acetate (50 ml) was added. The thus formed solution was washed with brine (50 ml), dried ($Na_2SO_4$) and the solvent was evaporated in vacuo. This afforded the title compound as an oil which was purified by column chromatography on silica gel (eluted with ethyl acetate containing 4% triethylamine). The title compound precipitated as its oxalate from acetone. Yield: 2.0 g, mp 233°–235° C.

In a corresponding manner the following indole derivative was prepared:

1-[1-[2-(3-Decanoylimidazolidin-2-on-1-yl)ethyl]-4piperidyl]-3-(4-fluorophenyl)-5-methyl-1H-indole, oxalate 21b, mp 175°–176° C.

EXAMPLE 22

Methyl 3-(4-fluorophenyl)-5-methyl-1H-indole-2-carboxylate 22a.

To a solution of p-toluidine (119.4 g) in conc. aqueous HCl (575 ml) was added a solution of $NaNO_2$ (84.6 g) in water (500 ml) at 0°–5° C. during 1.5 h. The reaction mixture was added in one portion to a mixture of methyl 2-(4-fluorobenzyl)-3-oxobutanoate (250 g), KOH (220 g), water (0.5 l), ethanol (1.25 l) and ice (2 kg) under stirring. After reaction for 2 h at room temperature the reaction mixture was extracted with diethyl ether (2×2 l). The combined organic phases were washed with water (3 l) and dried ($Na_2SO_4$). Evaporation of the solvents afforded the crude 4-tolylhydrazone of methyl 2-oxo-3-(4-fluorophenyl)-propanoate (330 g), which was used without further purification.

A mixture of the crude hydrazone, methanol (2.25 l) and aqueous $H_2SO_4$ (100 ml) was refluxed for 18 h. The reaction mixture was cooled to room temperature and a part of the solvents were evaporated in vacuo. The thus obtained solution was cooled to 0° C. and the precipitated compound was filtered off and dried overnight in vacuo. at 60° C. Yield: 180 g, mp 151°–155° C.

In a corresponding manner the following indole derivatives were prepared:

Methyl 5-chloro-3-(4-fluorophenyl)-1H-indole-2-carboxylate 22b, mp 184°–186° C.

Methyl 5-fluoro-3-(4-fluorophenyl)-1H-indole-2-carboxylate, 22c, (oil).

Methyl 3-(4-fluorophenyl)-1H-indole-2-carboxylate 22d, mp 148°–150° C.

Methyl 3-(4-fluorophenyl)-5-trifluoromethyl-1H-indole-2-carboxylate 22e, mp 136°–139° C.

Methyl 5-chloro-3-phenyl-1H-indole-2-carboxylate 22f, (oil).

EXAMPLE 23

Methyl 6-chloro-3-(4-fluorophenyl)-1H-indole-2-carboxylate 23a.

To a mixture of a 50% sodium hydride suspension in mineral oil (52.5 g) (which was extracted with dry heptane) and dry tetrahydrofuran (250 ml) was added a solution of N-benzoyl 5-chloro-2-(4-fluorobenzoyl)aniline (129 g) in dry tetrahydrofuran (500 ml) during 0.5 h at 20° C. (ice bath). After 1 h methyl 2-bromoacetate (101 ml) was added during 0.5 h at 20° C. (ice bath) and the mixture was stirred for another 1 hour. The solvents were evaporated in vacuo. The remaining oil was diluted with methanol (250 ml) and 5.4M sodium methoxide in methanol (670 ml) was added carefully. After 1 h at room temperature the solvents were evaporated in vacuo and water (0.5 l) was added. The thus obtained mixture was extracted with ethyl acetate (2×0.75 l) and the combined organic phases were washed with brine and dried ($Na_2SO_4$). Evaporation of the solvents in vacuo afforded the title compound, which was purified by column chromatography on silica gel (eluted with ethyl acetate/heptane 1:3) and crystallized from heptane. Yield: 33 g, mp 172°–183° C.

EXAMPLE 24

2,5-Dimethyl-3-(4-fluorophenyl)-1H-indole 24a.

A solution of 4-fluorophenylacetone (60 g), 4-tolylhydrazine, HCl (68.8 g) and triethylamine (165 ml)in ethanol (600 ml) was refluxed for 18 h. The reaction mixture was cooled to room temperature, the solvents were evaporated in vacuo and water (500 ml) was added to the remaining oil. The thus obtained mixture was extracted with ethyl acetate (2×250 ml). The combined organic phases were washed with brine and dried ($Na_2SO_4$). Evaporation of the solvents afforded the crude 4-fluorophenylacetone tolylhydrazone (100 g) as an oil, which was used without further purification.

The crude hydrazone (100 g), ethanol (700 ml) and conc. aqueous $H_2SO_4$ (40 ml) were refluxed for 18 h. After cooling to room temperature water (0.5 l) was added. The thus obtained mixture was extracted with (2×700 ml) ethyl acetate and the combined organic phases were washed with brine, dried and the solvents were evaporated in vacuo. This afforded the title compound, which was purified by column chromatography on silica gel (eluted with ethyl acetate/heptane 1:4) and crystallized from heptane. Yield: 75.5 g, mp:124°–128° C. In a corresponding manner the following indole derivative was prepared: 5-Chloro-3-phenyl-2-methyl-1H-indole 24b, (oil).

EXAMPLE 25

6-Chloro-3-(4-fluorophenyl)-1H-indazole 25a.

To solution of 5-chloro-2-(4-fluorobenzoyl)aniline (5 g) in 6M aqueous HCl (25 ml) was added a solution of $NaNO_2$ (2.5 g) in water (5 ml) at 0°–5° C. under stirring during 15 min. After stirring for further 0.5 h at 0° C. a solution of SnCl2 (20 g) in conc. aqueous HCl (25 ml) was added. The reaction mixture was allowed to heat to room temperature and after 0.5 h the precipitate was filtered off and suspended in 2 N aqueous NaOH. The suspension was filtered and dichloromethane was added to the precipitate. The thus obtained solution was washed with brine and dried ($MgSO_4$). Evaporation of the solvents afforded the title compound (2.5 g) as an oil which was used without further purification. In a corresponding manner the following indazole derivative was prepared: 3-(4-Fluorophenyl)-5-trifluoromethyl-1H-indazole 25b, (oil)

EXAMPLE 26

2-Bromo-3-(4-fluorophenyl)-1-(4-piperidyl)-1H-indole 26a.

A mixture of 2,2,2-trichloroethyl 4-[3-(4-fluorophenyl)-1H-indol-1-yl]piperidine-1-carboxylate 10b (4.0 g), N-bromosuccinimid (1.5 g) and tetrachloromethane (60 ml) was refluxed for 2 h. The reaction mixture was cooled to room temperature and the precipitate was filtered off. Evaporation of the solvent afforded the crude 2,2,2-trichloroethyl 2-bromo-4-[3-(4-fluorophenyl)-1H-indol-1-yl]piperidine-1-carboxylate (4.4 g) as an oil which was used without further purification. A mixture of the crude 2-bromo-indole (4.4 g), zinc powder (4.4 g) and 90% acetic acid in water (150 ml) was heated at 40° C. for 30 min. The reaction mixture was filtered and the solvent evaporated in vacuo. To the remaining oil was added ethyl acetate (50 ml) and the thus obtained solution was washed successively with water, 4N aqueous NaOH and brine. Evaporation of the solvents afforded the title compound as an oil (2.9 g).

EXAMPLE 27

2-Chloro-3-(4-fluorophenyl)-5-methyl-1-[1-[2-[3-(2-propyl)imidazolidin-2-on-1-yl]ethyl]-4-piperidyl]-1H-indole 27a.

A mixture of 3-(4-Fluorophenyl)-5-methyl-1-[1-[2-[3-(2-propyl)imidazolidin-2-on-1yl]ethyl]-4-piperidyl)-1H-indole 4h (3.0 g), dimethylsulphoxide (0.51 g) and conc. aqueous HCl (1 ml) was heated to 60° C. for 0.5 h under stirring. The reaction mixture was cooled to room temperature and water was added. The solution was extracted with ethyl acetate (2×50 ml). The combined organic phases were washed with 4N aqueous NaOH and brine. Evaporation of the solvent gave an oil which was purified by column chromatography on silica gel (eluted with ethyl acetate/heptane 1:3). This afforded the title compound which crystallized from diethyl ether. Yield 0.4 g, mp 127°–130° C.

PHARMACOLOGICAL TESTS

The compounds of the invention were tested in well recognized and reliable methods. The tests were as follows and the results are given in the following Table 1. The well known $5HT_2$ antagonists ritanserin and ICI 169369 were included in the tests for comparison purposes.

INHIBITION OF $^3$H-KETANSERIN BINDING TO SEROTONIN $S_2$ (5-$HT_2$) RECEPTORS IN RAT CORTEX IN VITRO

By this method the inhibition by drugs of the binding of $^3$H-Ketanserin (0,5 nM) to Serotonin $S_2$ (5-$HT_2$) receptors in membranes from rat is determined in vitro. Method in Hyttel, *Pharmacology & Toxicology*, 61, 126–129, 1987.

Procedure

Male Wistar (Mol:Wist) rats (125–250 g) are sacrificed and conical tissue is dissected and weighed. The tissue is homogenized (Ultra Turrax, 10 sec.) in 10 ml of ice-cold 50 mM tris buffer pH 7.7 (at 25° C.). The centrifuge glassware used in this step has been rinsed by sonication for 10 min. in ethanol. The homogenate is centrifuged twice at 20,000 g for 10 min. at 4° C. with rehomogenization of the pellet in 10 ml ice-cold buffer. The final pellet is homogenized in 500 vol (w/v)ice-cold buffer.

Incubation tubes kept on ice in triplicate receive 100 µl Of drug solution in water (or water for total binding) and 2000 µl of tissue suspension (final tissue content corresponds to 4 mg original tissue). The binding experiment is initiated by addition of 100 µl of $^3$H-Ketanserin (final concentration 0.5 nM) and by placing the tubes in a 37° C. water bath. After incubation for 30 min. the samples are filtered under vacuum (0–50 mBar) through Whatman GF/F filters (25 mm). The tubes are rinsed with 5 ml ice-cold buffer which are then poured on the filters. Thereafter, the filters are washed with 2×5 ml of buffer. The filters are placed in counting vials and 4 ml of appropriate scintillation fluid (e.g. Picofluor TM 15) are added. After shaking for 1 h and storage 2 hrs in the dark the content of radioactivity is determined by liquid scintillation counting. Specific binding is obtained by subtracting the nonspecific binding in the presence of 1 µM mianserin. For determination of the inhibition of binding five concentrations of drugs covering 3 decades are used.

The measured cpm are plotted against drug concentration on semilogarithmic paper and the best fitting S-shaped curve is drawn. The $IC_{50}$ value is determined as the concentration at which the binding is 50% of the total binding in control samples minus the nonspecific binding in the presence of 1 µM mianserin.

$^3$H-Ketanserin=[ethylene-$^3$H]-ketanserin hydrochloride from New England Nuclear, specific activity 60-80 Ci/mmol).

INHIBITION OF $^3$H-SPIPERONE BINDING TO DOPAMINE D-2 RECEPTORS IN RAT CORPUS STRIATUM IN VITRO

By this method the inhibition by drugs of the binding of $^3$H-spiperone (=$^3$H-spiroperidol) (0.5 nM) to dopamine D-2 receptors in membranes from rat corpus striatum is determined in vitro. Method and results in Hyttel & Larsen, *J. Neurochem*, 44, 1615-1622, 1985).

Procedure

Male Wistar (Mol:Wistar) rats (125-250 g) are sacrificed and striatal tissue is dissected and weighed. The tissue is homogenized (Ultra Turrax, 10 sec.) in 10 ml of ice-cold 50 mM K-phosphate buffer pH 7.4 (at 25° C.). The homogenate is centrifuged twice at 20,000 g for 10 min. at 4° C. with rehomogenization of the pellet in 10 ml ice-cold buffer. The final pellet is homogenized in 1300 vol (w/v) ice-cold buffer.

Incubation tubes kept on ice in triplicate receive 100 μl of drug solution in water (or water for total binding) and 4000 μl Of tissue suspension (final tissue content corresponds to 3.08 mg original tissue). The binding experimental is initiated by addition of 100 μl of $^3$H-spiperone (final concentration 0.5 nM) and by placing the tubes in a 37° C. water bath. After incubation for 10 min. the samples are filtered under vacuum (0-50 mBar) through Whatman GF/F filters (25 mm). The tubes are rinsed with 5 ml ice-cold buffer which are then poured on the filters. Thereafter, the filters are washed with 2×5 ml of buffer. The filters are placed in counting vials and 4 ml of appropriate scintillation fluid (e.g. Picofluor TM 15) are added. After shaking for 1 h and storage 2 hrs in the dark the content of radioactivity is determined by liquid scintillation counting. Specific binding is obtained by subtracting the nonspecific binding in the presence of 10 μM of 6,7-ADTN.

For determination of the inhibition of binding five concentrations of drugs covering 3 decades are used.

The measured cpm are plotted against drug concentration on semilogarithmic paper and the best fitting S-shaped curve is drawn. The IC$_{50}$ value is determined as the concentration at which the binding is 50% of the total binding in control samples minus the nonspecific binding in the presence of 10 μM of 6,7-ADTN. $^3$H-Spiperone=[phenyl-4-$^3$H]-spiperone from Amersham International plc. England, specific activity 15-25 Ci/mmol.

TABLE 1

| Compound | $^3$H-Ketanserin Binding IC$_{50}$ nM | $^3$H-Spiroperidol Binding IC$_{50}$ nM |
|---|---|---|
| 4a | 1.5 | 46 |
| 4b | 1.9 | 37 |
| 4c | 3.7 | 42 |
| 4d | 5.7 | 410 |
| 4e | 5.4 | 570 |
| 4f | 1.4 | 550 |
| 4g | 1.6 | 920 |
| 4h | 2.7 | 1100 |
| 4i | 1.4 | 680 |
| 4j | 4.5 | 1200 |
| 4k | 3.1 | 120 |
| 4l | 3.3 | 74 |
| 4m | 3.2 | 250 |
| 4n | 3.1 | 190 |
| 4o | 37 | 790 |
| 4p | 29 | 2800 |

TABLE 1-continued

| Compound | $^3$H-Ketanserin Binding IC$_{50}$ nM | $^3$H-Spiroperidol Binding IC$_{50}$ nM |
|---|---|---|
| 4q | 25 | 3000 |
| 4r | 3.4 | 230 |
| 4s | 12 | 330 |
| 4t | 38 | 1900 |
| 4u | 220 | 42000 |
| 4v | 11 | >1000 |
| 4x | 11 | 650 |
| 6a | 2.8 | 6300 |
| 6b | 3.8 | 710 |
| 6c | 1.4 | 320 |
| 6d | 4.4 | 32 |
| 6e | 9.4 | 1000 |
| 6f | 3.6 | 440 |
| 7a | 3.4 | 6900 |
| 7b | 6.2 | >1000 |
| 7c | 7.8 | 5300 |
| 9a | 5.3 | 2600 |
| 9b | 17 | 2900 |
| 11a | 4.5 | 540 |
| 13a | 3.7 | 250 |
| 13b | 2.3 | 260 |
| 15a | 1.8 | >1000 |
| 16a | 22 | 1500 |
| 18b | 4.3 | 1100 |
| 20a | 13 | 3900 |
| 21a | 18 | 890 |
| 27a | 10 | 3200 |
| Ritanserin | 0.4 | 12 |
| ICI 169369 | 15.0 | 490 |

It is seen from the table that the derivatives of the present invention which have been tested are all selective 5-HT$_2$ ligands, the affinity for the 5-HT$_2$ receptor as shown in the $^3$H-ketanserin binding test being very high as compared to the affinity for the dopamine D-2 receptor as measured in the $^3$H-spiroperidol binding test. As compared to the known standard 5-HT$_2$ antagonists ritanserin and ICI 169369 the compounds of the invention are in general found to be more selective.

Additionally the compounds of the invention were tested in the following well known and reliable in vivo tests:

QUIPAZINE INHIBITION

Quipazine is a 5-HT$_2$ agonist, which induces head twitches in rats. The test is a test for 5-HT$_2$-antagonistic effect testing the ability to inhibit head twitches. The method and test results for some reference substances are published by Arnt et al. (Drug Development Research, 16, 59-70, 1989).

ANTAGONISM OF PERGOLIDE-INDUCED CIRCLING BEHAVIOUR IN RATS WITH UNILATERAL 6-OHDA LESIONS

Dopamine D-2 agonists induce contralateral circling behaviour in rats with 6OHDA lesions. Pergolide-induced circling is antagonized by dopamine D-2 antagonists. (Arnt, J. and J. Hyttel, *Eur. J. Pharmacol.* 102, 349-354, 1984; Arnt, J. and J. Hyttel, *J. Neural Transm.* 67, 225-240, 1986). The test is an extremely sensitive test for dopamine D-2 antagonism in vivo.

These in vivo tests showed that the compounds of the invention are strong and selective 5-HT$_2$ antagonists with long duration of action in vivo (Quipazine test) and that they are substantially without dopamine D-2 antagonistic activity in vivo as shown in the test for antagonism of pergolide induced circling.

Accordingly, the compounds of the present invention are selective 5-HT$_2$ antagonist in vivo and in vitro thus being useful in the treatment of anxiety, depression, sleep disturbances, migraine, negative symptoms of schizophrenia, and Parkinson's Disease without neurological side effects as known from the classical neuroleptics.

FORMULATION EXAMPLES

The pharmaceutical formulations of the invention may be prepared by conventional methods in the art.

For example: Tablets may be prepared by mixing the active ingredient with ordinary adjuvants and/or diluents and subsequently compressing the mixture in a conventional tabletting machine. Examples of adjuvants or diluents comprise: corn starch, potato starch, talcum, magnesium stearate, gelatine, lactose, gums, and the like. Any other adjuvants or additives usually used for such purposes such as colourings, flavourings, preservatives etc. may be used provided that they are compatible with the active ingredients. Solutions for injections may be prepared by dissolving the active ingredient and possible additives in a pan of the solvent for injection, preferably sterile water, adjusting the solution to desired volume, sterilization of the solution and filling in suitable ampules or vials. Any suitable additive conventionally used in the art may be added, such as tonicity agents, preservatives, antioxidants, etc.

Typical examples of recipes for the formulation of the invention are as follows:

| 1) Tablets containing 5 milligrams of Compound 4c calculated as the free base: | |
|---|---|
| Comp. 4c | 5 mg |
| Lactose | 18 mg |
| Potato starch | 27 mg |
| Sucrose | 58 mg |
| Sorbitol | 3 mg |
| Talcum | 5 mg |
| Gelatine | 2 mg |
| Povidone | 1 mg |
| Magnesium stearate | 0.5 mg |

| 2) Tablets containing 50 milligrams of Compound 4b calculated as the free base: | |
|---|---|
| Comp. 4b | 50 mg |
| Lactose | 16 mg |
| Potato starch | 45 mg |
| Sucrose | 106 mg |
| Sorbitol | 6 mg |
| Talcum | 9 mg |
| Gelatine | 4 mg |
| Povidone | 3 mg |
| Magnesium stearate | 0.6 mg |

| 3) Syrup containing per milliliter: | |
|---|---|
| Comp. 4h | 10 mg |
| Sorbitol | 500 mg |
| Tragacanth | 7 mg |
| Glycerol | 50 mg |
| Methyl-paraben | 1 mg |
| Propyl-paraben | 0.1 mg |
| Ethanol | 0.005 ml |
| Water | ad 1 ml |

| 4) Solution for injection containing per milliliter: | |
|---|---|
| Comp. 4c | 50 mg |

| 4) Solution for injection containing per milliliter: | |
|---|---|
| Acetic acid | 17.9 mg |
| Sterile water | ad 1 ml |

| 5) Solution for injection containing per milliliter: | |
|---|---|
| Comp. 4h | 10 mg |
| Sorbitol | 42.9 mg |
| Acetic acid | 0.63 mg |
| Sodium hydroxide | 22 mg |
| Sterile water | ad 1 ml |

We claim:

1. A 3-arylindole compound selected from those having the formula:

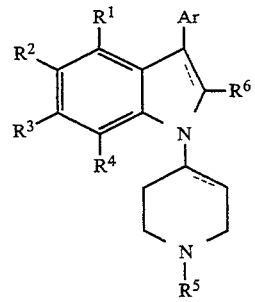

wherein Ar is phenyl optionally substituted with one or more substituents from halogen, lower alkyl, lower alkoxy, hydroxy, trifluoromethyl, and cyano;

$R^1$-$R^4$ are independently selected from hydrogen, halogen, lower alkyl, lower alkoxy, hydroxy, nitro, lower alkylthio, lower alkylsulphonyl, lower alkyl- or dialkyl amino, cyano, trifluoromethyl, and trifluoromethylthio;

the dotted lines designate optional double bonds;

$R^6$ is hydrogen, halogen, trifluoromethyl or lower alkyl;

$R^5$ is hydrogen, or cycloalkyl wherein the cycloalkyl is $C_{3-8}$, cycloalkylalkyl wherein the cycloalkyl is $C_{3-8}$ and the alkyl is $C_{1-4}$, lower alkyl or lower alkenyl, optionally substituted with one or two hydroxy groups, or $R^5$ is a group taken from structures 1a and 1b:

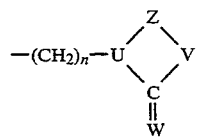

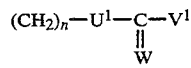

wherein n is an integer of 2-6, inclusive;

W is oxygen or sulfur;

U is nitrogen or CH;

Z is —$(CH_2)_m$—, m being 2 or 3, or Z is 1,2-phenylene optionally substituted with halogen or trifluoromethyl, or Z is —CH=CH—, —COCH$_2$—, or —CSCH$_2$—;

V is oxygen, sulphur, $CH_2$, or $NR^7$, wherein $R^7$ is hydrogen or lower alkyl or lower alkenyl, cycloalkyl wherein the cycloalkyl is $C_{3-8}$ or cycloalkylalkyl wherein the cycloalkyl is $C_{3-8}$ and the alkyl is $C_{1-4}$, optionally substituted with one or two hydroxy groups;

$U^1$ is oxygen, sulphur, $CH_2$, or a group $NR^8$, wherein $R^8$ is hydrogen or lower alkyl or lower alkenyl, cycloalkyl wherein the cycloalkyl is $C_{3-8}$ or cycloalkylalkyl wherein the cycloalkyl is $C_{3-8}$ and the alkyl is $C_{1-4}$, optionally substituted with one or two hydroxy groups; and $V^1$ is $NR^9R^{10}$, $OR^{11}$, $SR^{12}$, or $CR^{13}R^{14}R^{15}$, wherein each of $R^9$–$R^{15}$ is independently selected from among the $R^8$ substituents;

provided that $R^5$ may not be methyl when $R^1$–$R^4$ each are hydrogen, and Ar is phenyl;

or a pharmaceutically acceptable acid addition salts or a prodrugs thereof.

2. A compound according to claim 1, wherein Ar is selected from phenyl and phenyl substituted with halogen.

3. A compound according to claim 2, wherein $R^5$ is a group of the formula

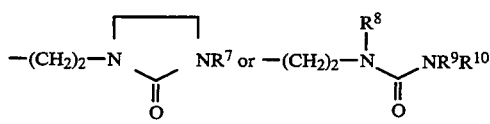

wherein $R^7$, $R^8$, $R^9$, and $R^{10}$ independently are selected from hydrogen, lower alkyl and lower alkenyl.

4. A compound according to claim 2, wherein either or both of $R^2$ and $R^6$ are other than hydrogen.

5. A compound according to claim 2, wherein $R^2$ is selected from halogen, —$CH_3$, and —$CF_3$ and $R^3$ is selected from hydrogen, halogen, —$CH_3$, and —$CF_3$.

6. A compound according to claim 1, wherein Ar is fluorophenyl.

7. A compound according to claim 1, wherein Ar is 4-fluorophenyl.

8. A compound selected from:
5-Chloro-3-(4-fluorophenyl)-1-[1-[2-(3-methylimidazolidin-2-on-1-yl)ethyl]-4-piperidyl]-1H-indole,
3-(4-Fluorophenyl)-1-[1-[2-(imidazolidin-2-on-1-yl)ethyl]-4-piperidyl]-5-methyl-1H-indole,
3-(4-Fluorophenyl)-5-methyl-1-[1-[2-[3-(2-propyl)imidazolidin-2-on-1-yl]ethyl]-4-piperidyl]-1H-indole,
2,5-Dimethyl-3-(4-fluorophenyl)-1-[1-[2-(imidazolidin-2-on-1-yl)ethyl]-1,2,3,6-tetrahydropyridin-4-yl]-1H-indole, 2,5-Dimethyl-3-(4-fluorophenyl)-1-[1-[2-(imidazolidin-2-on-1-yl)ethyl]-4-piperidyl]-1H-indole,
2,5-Dimethyl-3-(4-fluorophenyl)-1-(1-methyl-4-piperidyl)-1H-indole, and
1-[1-[2-(1,3-Dimethyl-1-ureido)ethyl]-4-piperidyl]-3-(4-fluorophenyl)-5-methyl-1H-indole.

9. A pharmaceutical preparation comprising a compound of claim 1 as an active ingredient together with a pharmaceutically acceptable carrier or diluent.

10. Method for treating a disease, selected from anxiety, aggression, negative symptoms of schizophrenia, depression, migraine, sleep disturbances, drug-induced Parkinsonism and Parkinsons disease comprising administration of a therapeutically effective amount of a compound of claim 1 to a patient in need thereof.

* * * * *